US012638669B2

(12) United States Patent
Inoue et al.

(10) Patent No.: US 12,638,669 B2
(45) Date of Patent: May 26, 2026

(54) ENDOSCOPE

(71) Applicant: FUJIFILM Corporation, Tokyo (JP)

(72) Inventors: Masaya Inoue, Kanagawa (JP);
Takashi Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 328 days.

(21) Appl. No.: 18/450,351

(22) Filed: Aug. 15, 2023

(65) Prior Publication Data

US 2023/0393382 A1     Dec. 7, 2023

Related U.S. Application Data

(63) Continuation of application No. PCT/JP2021/048343, filed on Dec. 24, 2021.

(30) Foreign Application Priority Data

Feb. 17, 2021     (JP) ................................. 2021-023408

(51) Int. Cl.
*A61B 1/00* (2006.01)
*A61B 1/008* (2006.01)
*G02B 23/24* (2006.01)
(52) U.S. Cl.
CPC .......... *G02B 23/2476* (2013.01); *A61B 1/008* (2013.01)

(58) Field of Classification Search
CPC ....... A61B 1/00; A61B 1/008; A61B 1/00105; A61B 1/0011; A61B 1/0052; A61B 1/01; G02B 23/2476; G02B 23/24
See application file for complete search history.

(56) References Cited

FOREIGN PATENT DOCUMENTS

| JP | H06125866 | 5/1994 |
| JP | H07178041 | 7/1995 |
| JP | H0984754 | 3/1997 |
| JP | 3181928 | 2/2013 |

OTHER PUBLICATIONS

"International Search Report (Form PCT/ISA/210) of PCT/JP2021/048343," mailed on Mar. 15, 2022, with English translation thereof, pp. 1-5. Searching Authority (Form PCT/ISA/237) of PCT/with English translation thereof, pp. 1-6.
"Written Opinion of The International JP2021/048343," mailed on Mar. 15, 2022.

*Primary Examiner* — Timothy J Neal
(74) *Attorney, Agent, or Firm* — JCIPRNET

(57) ABSTRACT

An endoscope includes first and second angle knobs that are connected to first and second wire pulling members which change a direction of a distal end of an insertion part, in which a rotational movement restricting member is attached instead of the first and second angle knobs before use. The rotational movement restricting member includes a first rotational movement restricting portion that is engaged with the first wire pulling member to restrict a rotational movement of the first wire pulling member and a second rotational movement restricting portion that is engaged with the second wire pulling member to restrict a rotational movement of the second wire pulling member.

7 Claims, 8 Drawing Sheets

ENDOSCOPE

CROSS-REFERENCE TO RELATED APPLICATIONS

This application is a Continuation of PCT International Application No. PCT/JP2021/048343 filed on 24 Dec. 2021, which claims priority under 35 U.S.C. § 119(a) to Japanese Patent Application No. 2021-023408 filed on 17 Feb. 2021. The above application is hereby expressly incorporated by reference, in its entirety, into the present application.

BACKGROUND OF THE INVENTION

1. Field of the Invention

The present invention relates to an endoscope.

2. Description of the Related Art

An endoscope for observing an inside of a body as an observation target is widely known. The endoscope comprises an insertion part to be inserted into the body as the observation target and an operation part that is consecutively provided at a proximal end part of the insertion part. The operation part is provided with a wire pulling member that pulls a wire disposed inside the insertion part in conjunction with a rotational movement to change a direction of a distal end of the insertion part, and an angle knob that is connected to the wire pulling member and transmits an operating force to the wire pulling member, and the direction of the distal end of the insertion part can be changed through a rotational movement operation of the angle knob.

As described in JP1997-084754A (JP9-084754A) below, some endoscopes are provided with an angle knob that is attachably and detachably provided with respect to an operation part. In such an endoscope, for example, the endoscope is shipped in a state in which the angle knob is detached from the operation part, and the angle knob is attached to the operation part for use. In this way, by attachably and detachably providing the angle knob, for example, it is possible to prepare a plurality of types of angle knobs having different outer diameters and allow a user to select which angle knob to attach and use. By doing so, the user can select the operating force required to bend a bending part depending on which angle knob to attach. In addition, JP3181928U describes an attachment to be placed over an angle knob. In this way, by placing the attachment over the angle knob, it is also possible to reduce the operating force required to bend the bending part.

SUMMARY OF THE INVENTION

However, in the conventional endoscopes, there has been a problem such as the insertion part being bent and the wire pulling member rotationally moving in a stage before use, such as during shipment or storage.

The present invention has been made in view of the above background, and an object of the present invention is to provide an endoscope that prevents the wire pulling member from rotationally moving in a stage before use.

In order to achieve the above object, according to an aspect of the present invention, there is provided an endoscope comprising: an insertion part to be inserted into a body as the observation target; a wire pulling member that pulls a wire disposed inside the insertion part in conjunction with a rotational movement to change a direction of a distal end of the insertion part; and an angle knob that is connected to the wire pulling member and transmits an operating force to the wire pulling member, in which the angle knob is detached from the wire pulling member in a stage before use and is attached to the wire pulling member for use, and the endoscope further comprises a rotational movement restricting member that is engaged with the wire pulling member in a state in which the angle knob is detached from the wire pulling member to restrict the rotational movement of the wire pulling member and to hold the wire pulling member in a predetermined rotational position.

For use, the rotational movement restricting member may be detached, and the angle knob may be attached instead.

The rotational movement restricting member may be provided so as to be movable between a rotational movement restricting position where the rotational movement restricting member is engaged with the wire pulling member to restrict the rotational movement of the wire pulling member and a rotational movement allowing position where the engagement is released and the rotational movement of the wire pulling member is allowed, and the rotational movement restricting member may move from the rotational movement restricting position to the rotational movement allowing position by being pressed by the angle knob in a process of attaching the angle knob to the wire pulling member.

The wire pulling member may be guided to the predetermined rotational position by being pressed by the rotational movement restricting member in a process of attaching the rotational movement restricting member.

The wire may consist of a first wire that is pulled to allow the distal end of the insertion part to face a first direction, a second wire that is pulled to allow the distal end of the insertion part to face a second direction opposite to the first direction, a third wire that is pulled to allow the distal end of the insertion part to face a third direction perpendicular to the first direction, and a fourth wire that is pulled to allow the distal end of the insertion part to face a fourth direction opposite to the third direction, the wire pulling member may consist of a first wire pulling member that is connected to the first and second wires and that selectively pulls one of the first and second wires according to a rotation direction, and a second wire pulling member that is connected to the third and fourth wires and that selectively pulls one of the third and fourth wires according to a rotation direction, and the angle knob may consist of a first angle knob that is connected to the first wire pulling member and a second angle knob that is connected to the second wire pulling member.

The rotational movement restricting member may include a first rotational movement restricting portion that restricts a rotational movement of the first wire pulling member and a second rotational movement restricting portion that restricts a rotational movement of the second wire pulling member, and restriction on the rotational movement of one of the first and second wire pulling members may be released so that restriction on the rotational movement of the other is also released.

The rotational movement restricting member may consist of a first rotational movement restricting member that restricts a rotational movement of the first wire pulling member and a second rotational movement restricting member that restricts a rotational movement of the second wire pulling member, in attaching the first angle knob, restriction on the rotational movement of the first wire pulling member by the first rotational movement restricting member is released, and in attaching the second angle knob, restriction on the rotational movement of the second wire pulling member by the second rotational movement restricting member is released.

According to the present invention, it is possible to provide an endoscope that prevents the wire pulling member from rotationally moving in a stage before use.

DESCRIPTION OF THE PREFERRED EMBODIMENTS

First Embodiment

Figure 1:
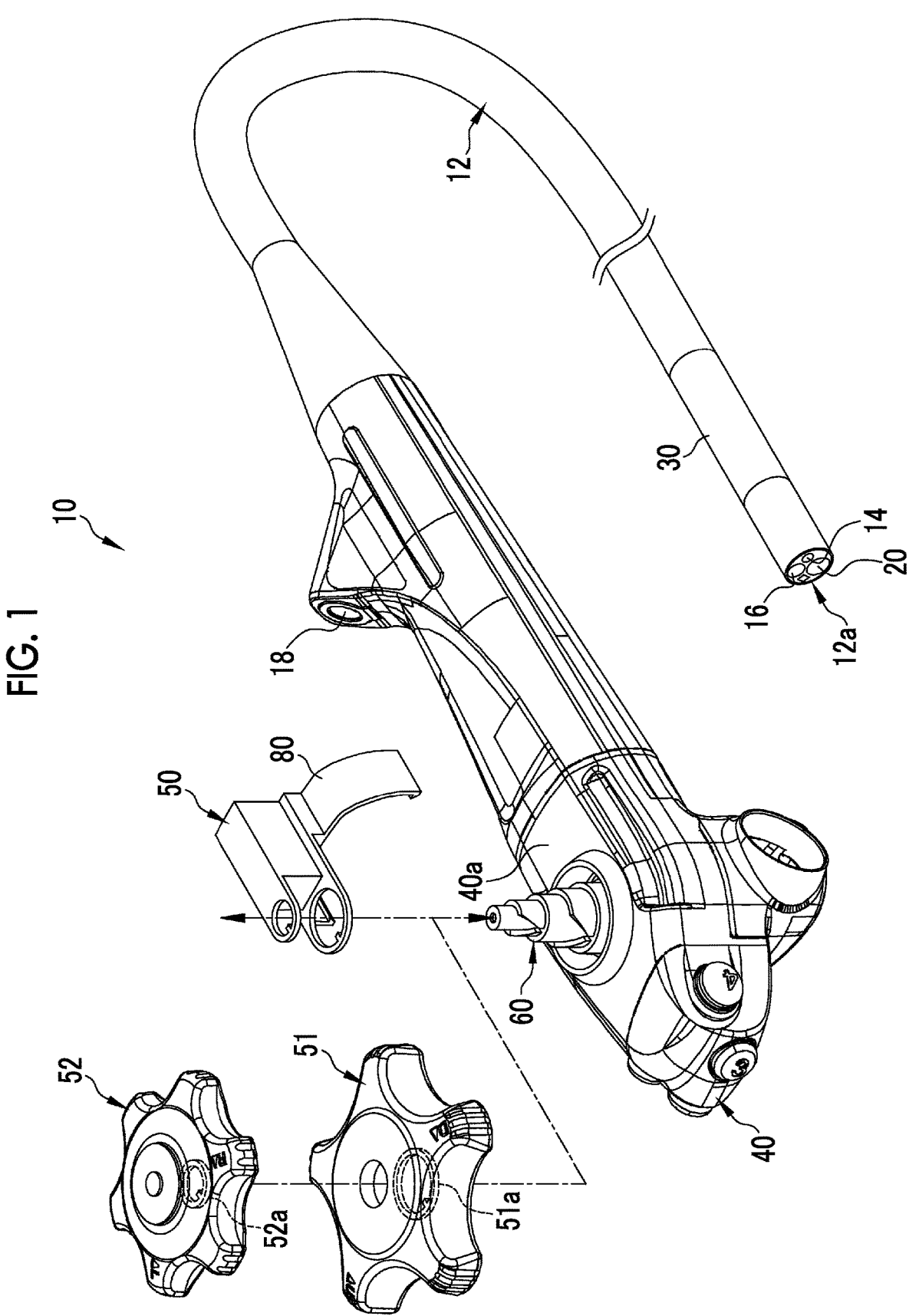
FIG. 1 is an external view of an endoscope.

In FIG. 1, an endoscope 10 comprises an insertion part 12 to be inserted into a body as an observation target. A distal end 12a of the insertion part 12 is provided with an illumination window 14 through which illumination light is emitted, an observation window 16 on which reflected light from the observation target is incident, and a forceps outlet 20 which is an outlet of a treatment tool such as a forceps inserted into the insertion part 12 through a forceps port 18.

A bending part 30 is provided in the vicinity of the distal end 12a of the insertion part 12. The bending part 30 is provided so as to be bendable up, down, left, and right. Four first to fourth wires 31 to 34 (see FIGS. 2 and 3) disposed inside the insertion part 12 are connected to the bending part 30. Then, the bending part 30 is bent in a first direction (upward direction in the present embodiment) by pulling the first wire 31 toward a proximal end side of the insertion part 12. In addition, the bending part 30 is bent in a second direction (downward direction in the present embodiment) by pulling the second wire 32 toward the proximal end side of the insertion part 12. Further, the bending part 30 is bent in a third direction (leftward direction in the present embodiment) by pulling the third wire 33 toward the proximal end side of the insertion part 12. Further, the bending part 30 is bent in a fourth direction (rightward direction in the present embodiment) by pulling the fourth wire 34 toward the proximal end side of the insertion part 12.

An operation part 40 is connected to the proximal end side of the insertion part 12. A rotational movement restricting member 50 is attached to the operation part 40 before the endoscope 10 is used, and for use, the rotational movement restricting member 50 is detached, and first and second angle knobs 51 and 52 are attached instead. The operation part 40 is provided with a wire pulling mechanism 60, and the first and second angle knobs 51 and 52 are attached to the wire pulling mechanism 60.

The wire pulling mechanism 60 comprises a first wire pulling member 61 (see FIGS. 2 and 3) to which the first and second wires 31 and 32 are connected, and the first angle knob 51 is connected to the first wire pulling member 61 by being attached to the first wire pulling member 61. Then, the first angle knob 51 is rotated in one direction (counterclockwise in the present embodiment) to pull the first wire 31 so that the distal end 12a of the insertion part 12 can be directed upward, and the first angle knob 51 is rotated in an opposite direction (clockwise in the present embodiment) to pull the second wire 32 so that the distal end 12a of the insertion part 12 can be directed downward.

In addition, the wire pulling mechanism 60 comprises a second wire pulling member 62 (see FIGS. 2 and 3) to which the third and fourth wires 33 and 34 are connected, and the second angle knob 52 is connected to the second wire pulling member 62 by being attached to the second wire pulling member 62. Then, the second angle knob 52 is rotated in one direction (counterclockwise in the present embodiment) to pull the third wire 33 so that the distal end 12a of the insertion part 12 can be directed leftward, and the second angle knob 52 is rotated in an opposite direction (clockwise in the present embodiment) to pull the fourth wire 34 so that the distal end 12a of the insertion part 12 can be directed rightward.

Figure 2:
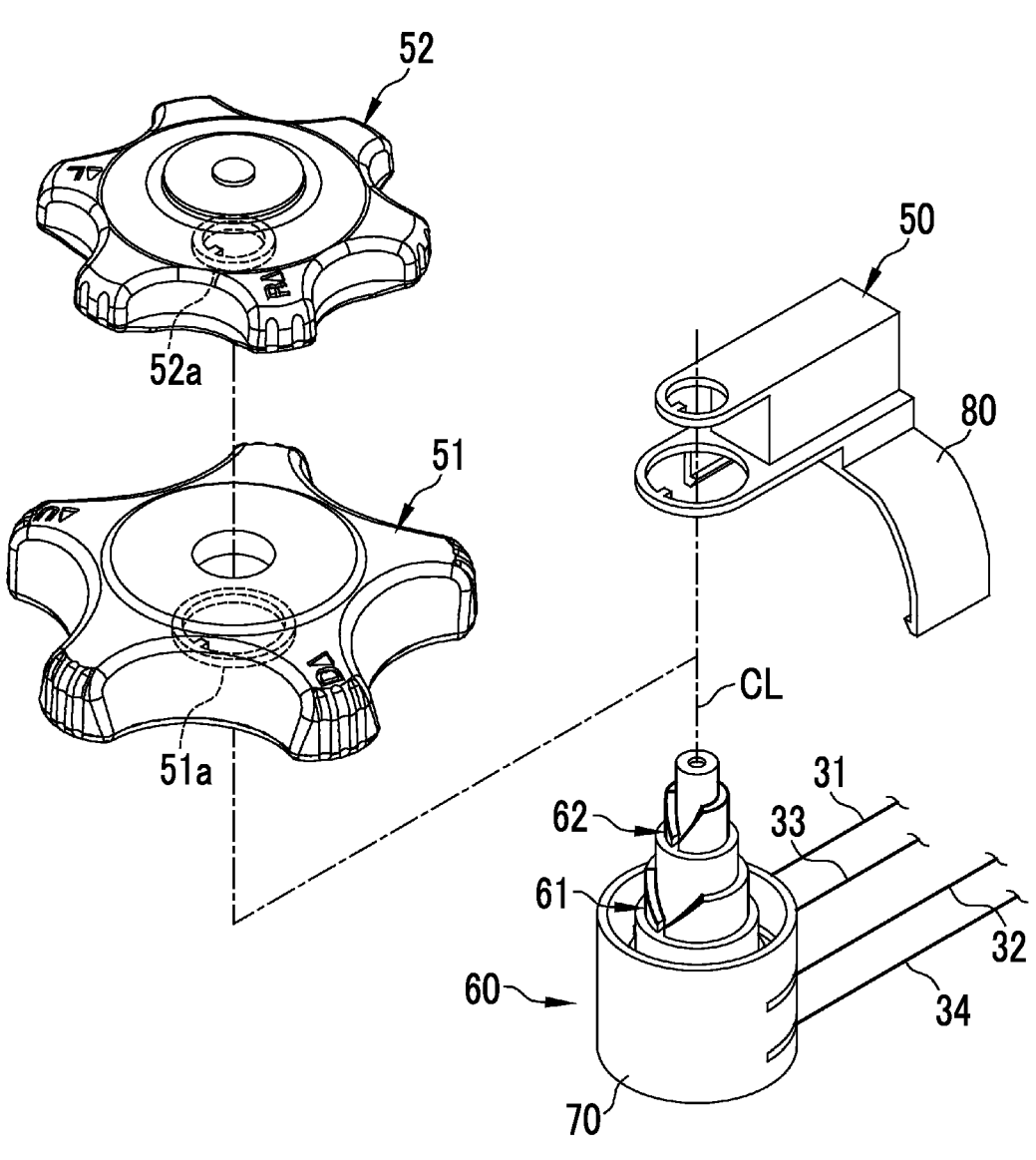
FIG. 2 is an external view of a wire pulling mechanism.
Figure 3:
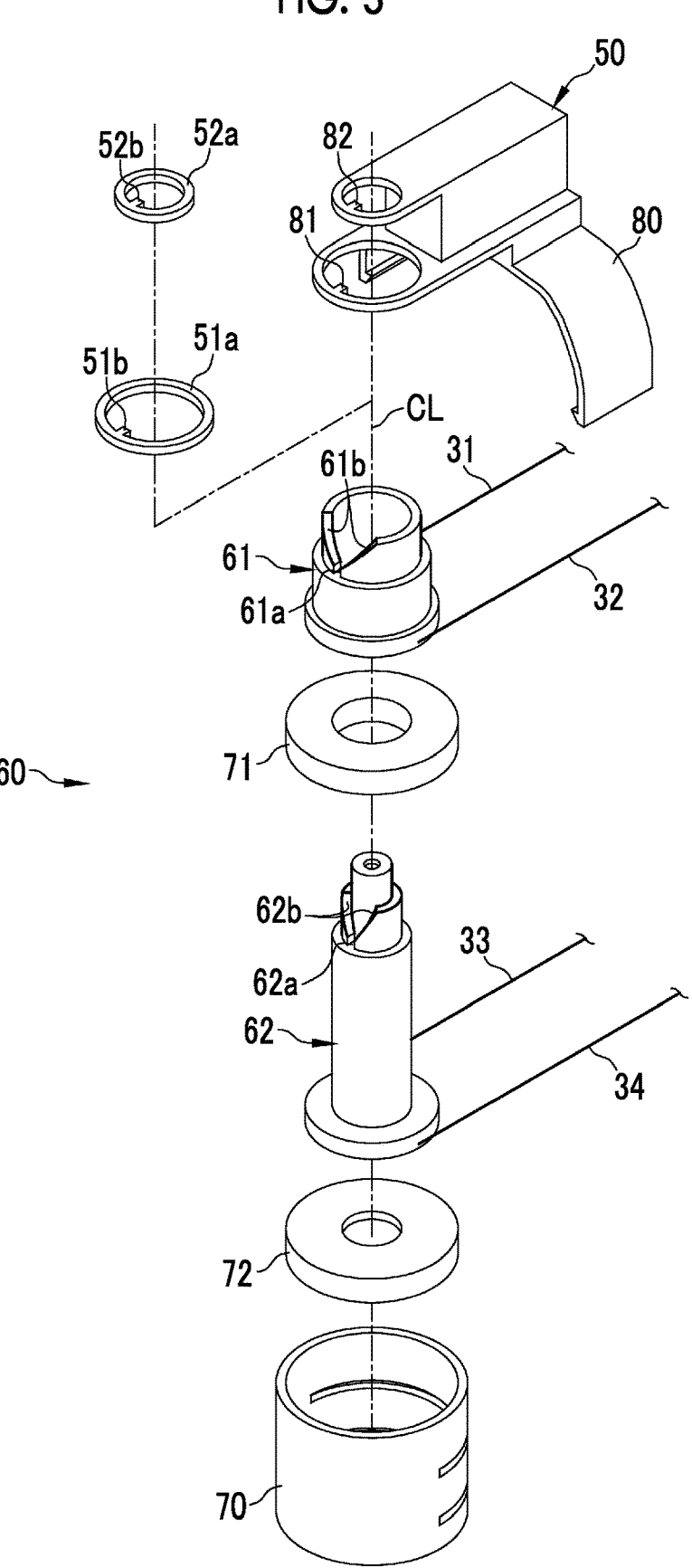
FIG. 3 is an exploded view of the wire pulling mechanism.

As shown in FIGS. 2 and 3, in the wire pulling mechanism 60, the first and second wire pulling members 61 and 62 described above are housed in a tube body 70 and are supported so as to be rotationally movable about an axis CL. The tube body 70 supports from an outer peripheral side a middle plate 71 on which the first wire pulling member 61 is placed and a bottom plate 72 on which the second wire pulling member 62 is placed. The first wire pulling member 61 is formed in a tubular shape, and the second wire pulling member 62 is formed in a shaft shape. The second wire pulling member 62 penetrates through the middle plate 71 and the first wire pulling member 61, and an upper part thereof protrudes upward of the tube body 70.

The first wire 31 and the second wire 32 are attached to a lower outer periphery of the first wire pulling member 61 at positions facing each other with the axis CL interposed therebetween, and the first wire pulling member 61 rotates counterclockwise about the axis CL to pull the first wire 31 and rotates clockwise to pull the second wire 32.

A first engagement groove 61a and a first guide groove 61b are formed on an upper part of the first wire pulling member 61. In a case where the first angle knob 51 is attached to the operation part 40, a first protrusion 51b of a first engagement ring 51a provided at a lower end of the first angle knob 51 is engaged with the first engagement groove 61a, and the first angle knob 51 and the first wire pulling member are connected to each other. As a result, the first angle knob 51 and the first wire pulling member 61 rotationally move integrally.

Meanwhile, in a case where the rotational movement restricting member 50 is attached to the operation part 40, a protrusion-like first rotational movement restricting portion 81 provided on the rotational movement restricting member 50 is engaged with the first engagement groove 61a. The rotational movement restricting member 50 comprises a holder that is fitted to an outer shell 40a (see FIG. 1) of the operation part 40, and in a case where the rotational movement restricting member 50 is attached to the operation part 40, the holder is fitted to the outer shell 40a, and the rotational movement restricting member 50 (the first rotational movement restricting portion 81) is held in a predetermined position and orientation. As a result, the rotational movement of the first wire pulling member 61 is restricted by the first rotational movement restricting portion 81 engaged with the first engagement groove 61*a*, and the first wire pulling member 61 is held in a predetermined rotational position.

The first guide groove 61*b* is a groove that is consecutively provided on an upper end side of the first engagement groove 61*a* and that is formed to be wider upward, and has a function of guiding (rotating) the first wire pulling member 61 to the predetermined rotational position described above (a position where the first engagement groove 61*a* is engaged with the first rotational movement restricting portion 81 in a state in which the rotational movement restricting member 50 is attached to the operation part 40) in a process of attaching the rotational movement restricting member 50 to the operation part 40. That is, even in a case where the first wire pulling member 61 is in a rotational position different from the predetermined rotational position described above in attaching the rotational movement restricting member 50, the first rotational movement restricting portion 81 presses against a side wall of the first guide groove 61*b* to rotate the first wire pulling member 61 to the predetermined rotational position described above in the process of attaching the rotational movement restricting member 50. This makes it convenient for the user to attach the rotational movement restricting member 50 without the need to adjust the rotational position of the first wire pulling member 61.

Similarly, the third wire 33 and the fourth wire 34 are attached to a lower outer periphery of the second wire pulling member 62 at positions facing each other with the axis CL interposed therebetween, and the second wire pulling member 62 rotates counterclockwise about the axis CL to pull the third wire 33 and rotates clockwise to pull the fourth wire 34.

A second engagement groove 62*a* and a second guide groove 62*b* are formed on the upper part of the second wire pulling member 62. In a case where the second angle knob 52 is attached to the operation part 40, a second protrusion 52*b* of a second engagement ring 52*a* provided at a lower end of the second angle knob 52 is engaged with the second engagement groove 62*a*, and the second angle knob 52 and the second wire pulling member 62 are connected to each other. As a result, the second angle knob 52 and the second wire pulling member 62 rotationally move integrally.

Meanwhile, in a case where the rotational movement restricting member 50 is attached to the operation part 40, a protrusion-like second rotational movement restricting portion 82 provided on the rotational movement restricting member 50 is engaged with the second engagement groove 62*a*. As described above, the rotational movement restricting member 50 comprises the holder 80 that is fitted to the outer shell 40*a* of the operation part 40, and in a case where the rotational movement restricting member 50 is attached to the operation part 40, the holder 80 is fitted to the outer shell 40*a*, and the rotational movement restricting member 50 (the second rotational movement restricting portion 82) is held in a predetermined position and orientation. As a result, the rotational movement of the second wire pulling member 62 is restricted by the second rotational movement restricting portion 82 engaged with the second engagement groove 62*a*, and the second wire pulling member 62 is held in a predetermined rotational position.

The second guide groove 62*b* is a groove that is consecutively provided on an upper end side of the second engagement groove 62*a* and that is formed to be wider upward, and has a function of guiding (rotating) the second wire pulling member 62 to the predetermined rotational position described above (a position where the second engagement groove 62*a* is engaged with the second rotational movement restricting portion 82 in a state in which the rotational movement restricting member 50 is attached to the operation part 40) in a process of attaching the rotational movement restricting member 50 to the operation part 40. That is, even in a case where the second wire pulling member 62 is in a rotational position different from the predetermined rotational position described above in attaching the rotational movement restricting member 50, the second rotational movement restricting portion 82 presses against a side wall of the second guide groove 62*b* to rotate the second wire pulling member 62 to the predetermined rotational position described above in the process of attaching the rotational movement restricting member 50. This makes it convenient for the user to attach the rotational movement restricting member 50 without the need to adjust the rotational position of the second wire pulling member 62.

In the above embodiment, an example has been described in which the groove (first and second guide grooves 61*b* and 62*b*) formed to be narrower downward (in a direction in which the rotational movement restricting member is attached to the endoscope) is used to rotate (guide) the wire pulling member to the predetermined rotational position in a process of attaching the rotational movement restricting member, but the present invention is not limited thereto. For example, a configuration may be employed in which the width of the groove is made constant, the width of the protrusion to be engaged with this groove is formed to be narrower downward (in a direction in which the rotational movement restricting member is attached to the endoscope), and the wire pulling member is rotated (guided) to the predetermined rotational position in the process of attaching the rotational movement restricting member.

Further, in the present invention, since the rotational movement restricting member that restricts the rotational movement of the wire pulling member in a state in which the angle knob is detached need only be provided, the detailed configuration is not limited to the above embodiment and can be appropriately changed. For example, in the above embodiment, an example has been described in which the protrusion provided on the rotational movement restricting member is engaged with the groove provided on the wire pulling member so that the rotational movement of the wire pulling member is restricted, but a configuration may be employed in which a groove provided on the rotational movement restricting member is engaged with a protrusion provided on the wire pulling member so that the rotational movement of the wire pulling member is restricted.

In addition, in the above embodiment, a configuration has been described as an example in which the rotational movements of the first and second wire pulling members 61 and 62 are restricted and released at the same time by attaching and detaching one rotational movement restricting member 50, but the present invention is not limited thereto. A configuration may be employed in which two rotational movement restricting members, that is, a first rotational movement restricting member that restricts and releases the rotational movement of the first wire pulling member 61 and a second rotational movement restricting member that restricts and releases the rotational movement of the second wire pulling member 62, are provided and the rotational movements of the first and second wire pulling members 61 and 62 are individually restricted and released.

Second Embodiment

In the above first embodiment, a configuration is employed in which the rotational movement restricting member 50 is attached to and detached from the outer shell 40*a* of the operation part 40, but in the second embodiment, the rotational movement restricting member (first and second rotational movement restricting members 121 and 122 (see FIG. 5)) are incorporated into the operation part 40 (a wire pulling mechanism 100 (see FIGS. 4 and 5)). Hereinafter, the second embodiment having such a configuration will be described with reference to FIGS. 4 to 9. In the following description, the same members as those in the first embodiment are designated by the same reference numerals, and the description thereof will be omitted.

Figure 4:
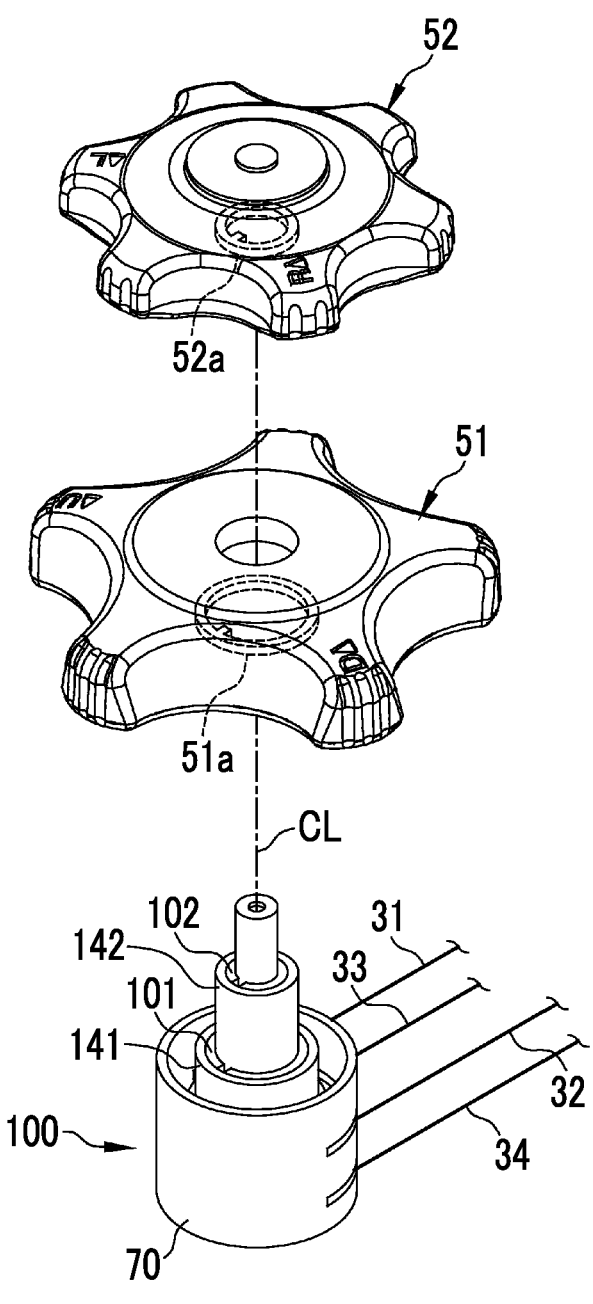
FIG. 4 is an external view of the wire pulling mechanism.
Figure 5:
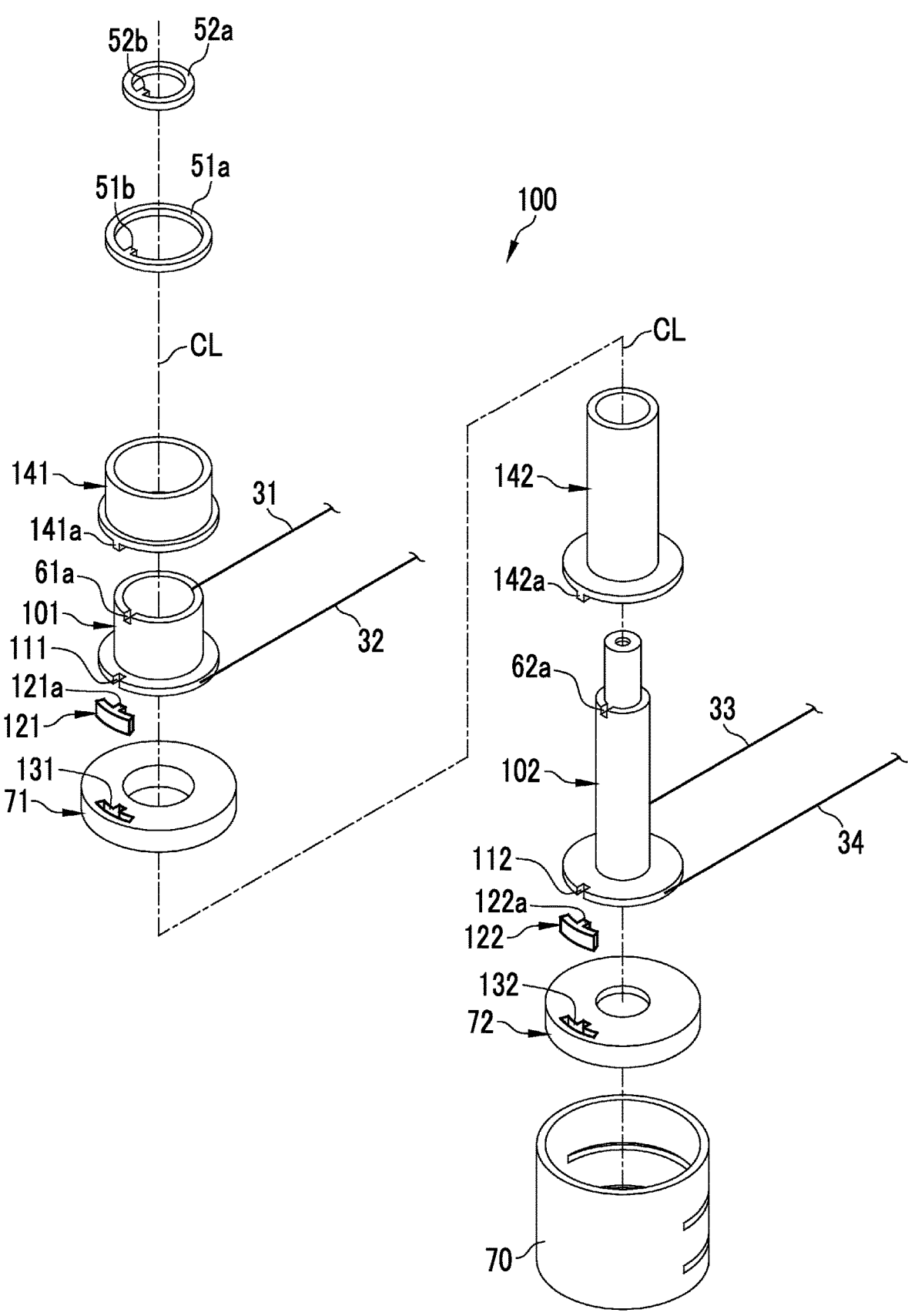
FIG. 5 is an exploded view of the wire pulling mechanism.

As shown in FIGS. 4 and 5, the wire pulling mechanism 100 of the second embodiment comprises a tubular first wire pulling member 101 that is placed on the middle plate 71 and that is provided so as to be rotationally movable about the axis CL. The first engagement groove 61*a* is provided on an upper part of the first wire pulling member 101, and in a case where the first angle knob 51 is attached to the first wire pulling member 101, the first engagement groove 61*a* and the first protrusion 51*b* are engaged with each other, and the first angle knob 51 and the first wire pulling member 101 are connected to each other. As a result, the first angle knob 51 and the first wire pulling member 101 rotationally move integrally.

A first rotational movement restricting groove 111 is formed on a lower part of the first wire pulling member 101. A first rotational movement restricting protrusion 121*a* provided on a first rotational movement restricting member 121 is engaged with the first rotational movement restricting groove 111. The first rotational movement restricting member 121 is supported so as to be vertically slidable through a vertically long first slide hole 131 formed in the middle plate 71. The first rotational movement restricting member 121 moves between a rotational movement restricting position (see FIG. 6) where the rotational movement of the first wire pulling member 101 is restricted by making an upper part of the first rotational movement restricting member 121 protrude from the first slide hole 131 and engaging the first rotational movement restricting protrusion 121*a* with the first rotational movement restricting groove 111 and a rotational movement allowing position (see FIG. 7) where the restriction on the rotational movement of the first wire pulling member 101 is released (the rotational movement is allowed) by accommodating the first rotational movement restricting member 121 inside the first slide hole 131.

A tubular first release member 141 is provided on an outer periphery of the first wire pulling member 101 so as to be slidable in a direction of the axis CL (vertical direction). A first release protrusion 141*a* that is inserted into the first rotational movement restricting groove 111 is provided at a lower end of the first release member 141.

Figure 6:
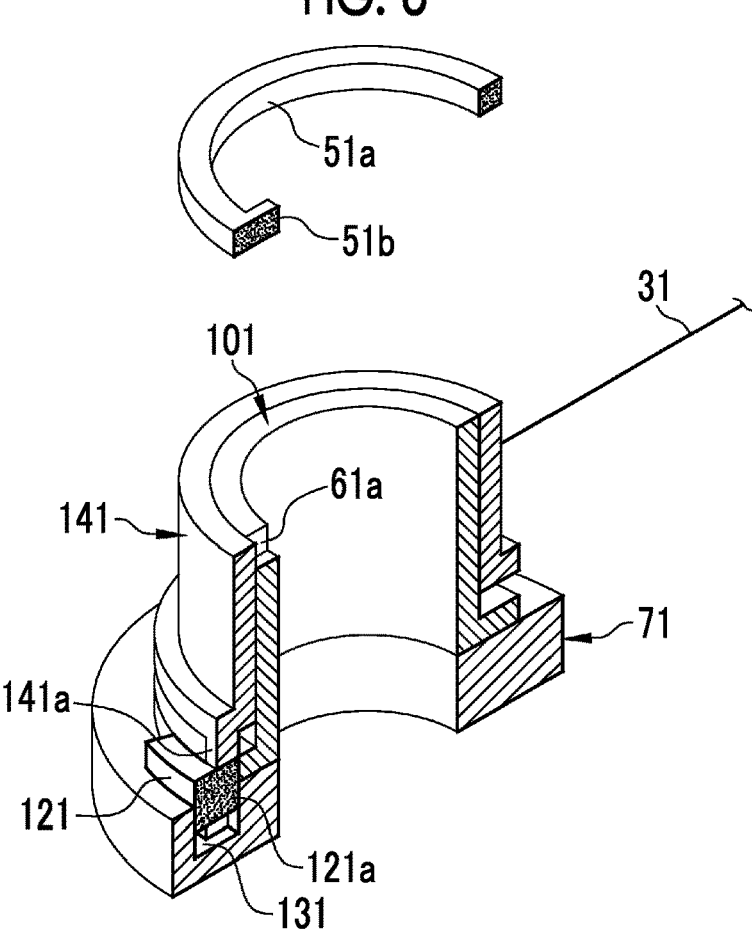
FIG. 6 is a diagram illustrating a mechanism in which rotational movement restriction of the wire pulling member is released in a process of attaching an angle knob.

As shown in FIG. 6, before the endoscope 10 is used, the first rotational movement restricting member 121 is set to the rotational movement restricting position, and the first rotational movement restricting protrusion 121*a* is engaged with the first rotational movement restricting groove 111. As a result, the rotational movement of the first wire pulling member 101 is restricted. Meanwhile, in this state, the first release protrusion 141*a* is disposed above the first rotational movement restricting protrusion 121*a*.

Figure 7:
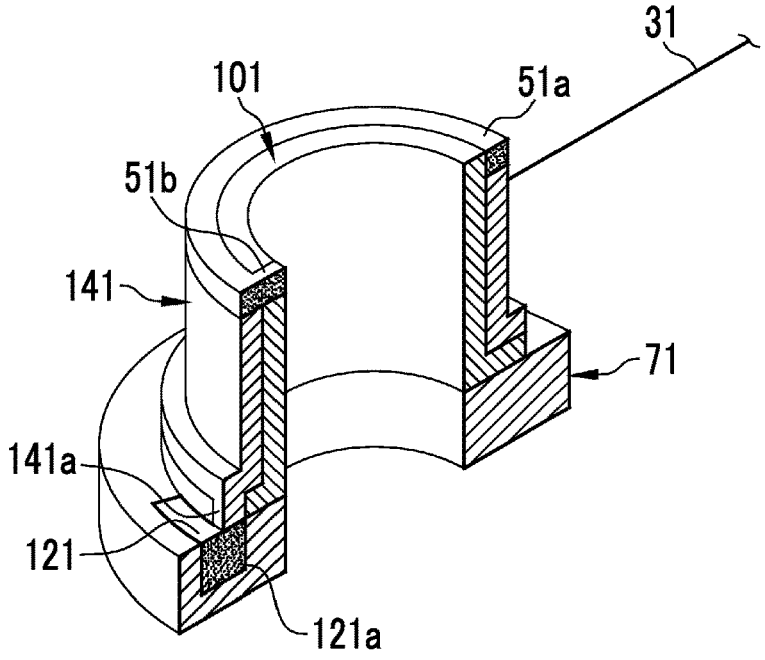
FIG. 7 is a diagram illustrating a mechanism in which rotational movement restriction of the wire pulling member is released in a process of attaching the angle knob.

As shown in FIG. 7, in a case where the first angle knob 51 is attached to the first wire pulling member 101 for the use of the endoscope 10, the first rotational movement restricting member 121 moves downward by being pressed by the first engagement ring 51*a* in the process of this attachment. Due to this movement, the first release protrusion 141*a* presses against the first rotational movement restricting protrusion 121*a* to move the first rotational movement restricting member 121 to the rotational movement allowing position. As a result, the restriction on the rotational movement of the first wire pulling member 101 is released. As described above, in the second embodiment, in the process of attaching the first angle knob 51, not only is the first angle knob 51 connected to the first wire pulling member 101, but also the restriction on the rotational movement of the first wire pulling member 101 is released at the same time.

Similarly, in FIGS. 4 and 5, the wire pulling mechanism 100 of the second embodiment comprises a shaft-like second wire pulling member 102 that is placed on the bottom plate 72 and that is provided so as to be rotationally movable about the axis CL. The second wire pulling member 102 and a second release member 142, which will be described later, penetrate through the middle plate 71, the first wire pulling member 101, and the first release member 141, and an upper part thereof protrudes upward of the tube body 70. The second engagement groove 62*a* is provided on an upper part of the second wire pulling member 102, and in a case where the second angle knob 52 is attached to the second wire pulling member 102, the second engagement groove 62*a* and the second protrusion 52*b* are engaged with each other, and the second angle knob 52 and the second wire pulling member 102 are connected to each other. As a result, the second angle knob 52 and the second wire pulling member 102 rotationally move integrally.

A second rotational movement restricting groove 112 is formed on a lower part of the second wire pulling member 102. A second rotational movement restricting protrusion 122*a* provided on a second rotational movement restricting member 122 is engaged with the second rotational movement restricting groove 112. The second rotational movement restricting member 122 is supported so as to be vertically slidable through a vertically long second slide hole 132 formed in the bottom plate 72. The second rotational movement restricting member 122 moves between a rotational movement restricting position where the rotational movement of the second wire pulling member 102 is restricted by making an upper part of the second rotational movement restricting member 122 protrude from the second slide hole 132 and engaging the second rotational movement restricting protrusion 122*a* with the second rotational movement restricting groove 112 and a rotational movement allowing position where the restriction on the rotational movement of the second wire pulling member 102 is released (the rotational movement is allowed) by accommodating the second rotational movement restricting member 122 inside the second slide hole 132.

A tubular second release member 142 is provided on an outer periphery of the second wire pulling member 102 so as to be slidable in the direction of the axis CL (vertical direction). A second release protrusion 142*a* that is inserted into the second rotational movement restricting groove 112 is provided at a lower end of the second release member 142.

Figure 8:
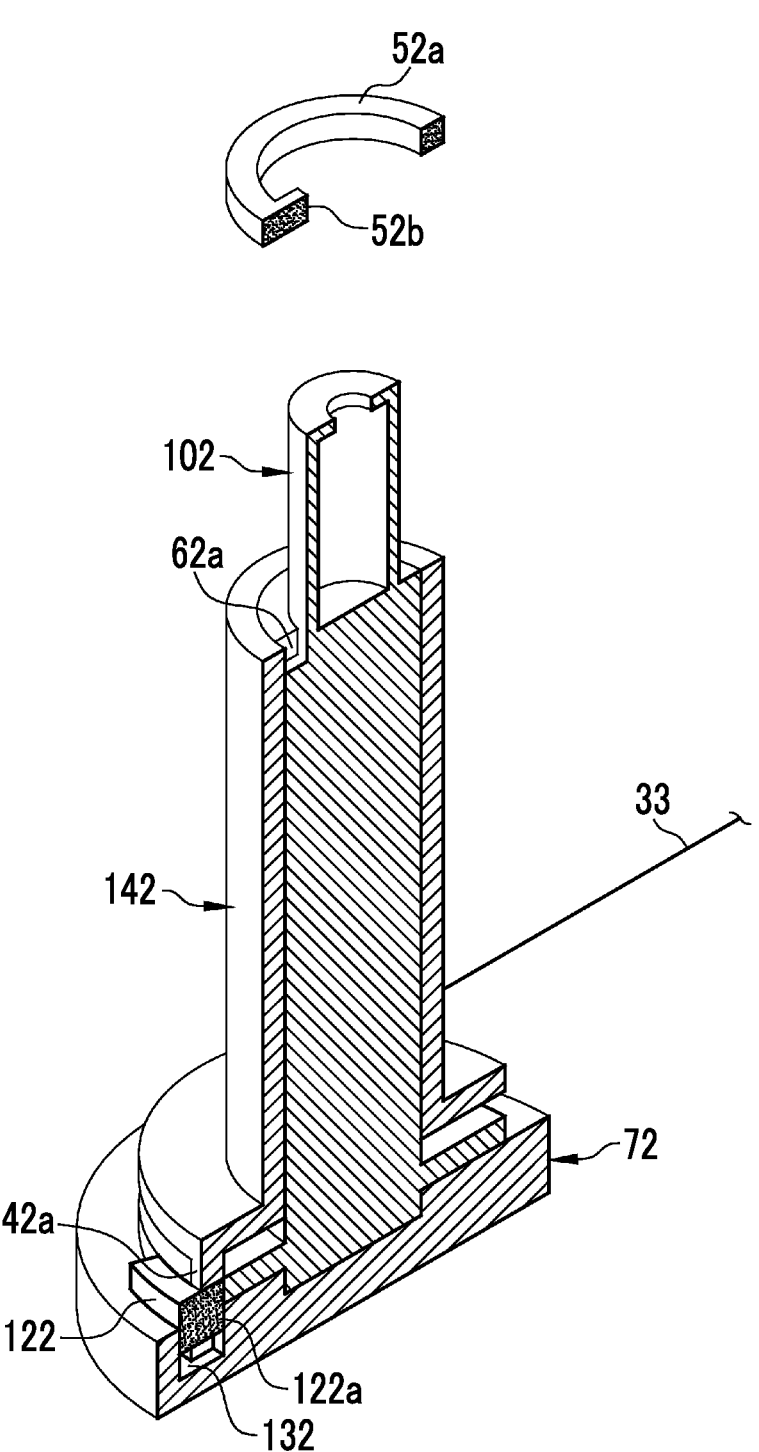
FIG. 8 is a diagram illustrating a mechanism in which rotational movement restriction of the wire pulling member is released in a process of attaching the angle knob.

As shown in FIG. 8, before the endoscope 10 is used, the second rotational movement restricting member 122 is set to the rotational movement restricting position, and the second rotational movement restricting protrusion 122*a* is engaged with the second rotational movement restricting groove 112. As a result, the rotational movement of the second wire pulling member 102 is restricted. Meanwhile, in this state, the second release protrusion 142a is disposed above the second rotational movement restricting protrusion 122a.

Figure 9:
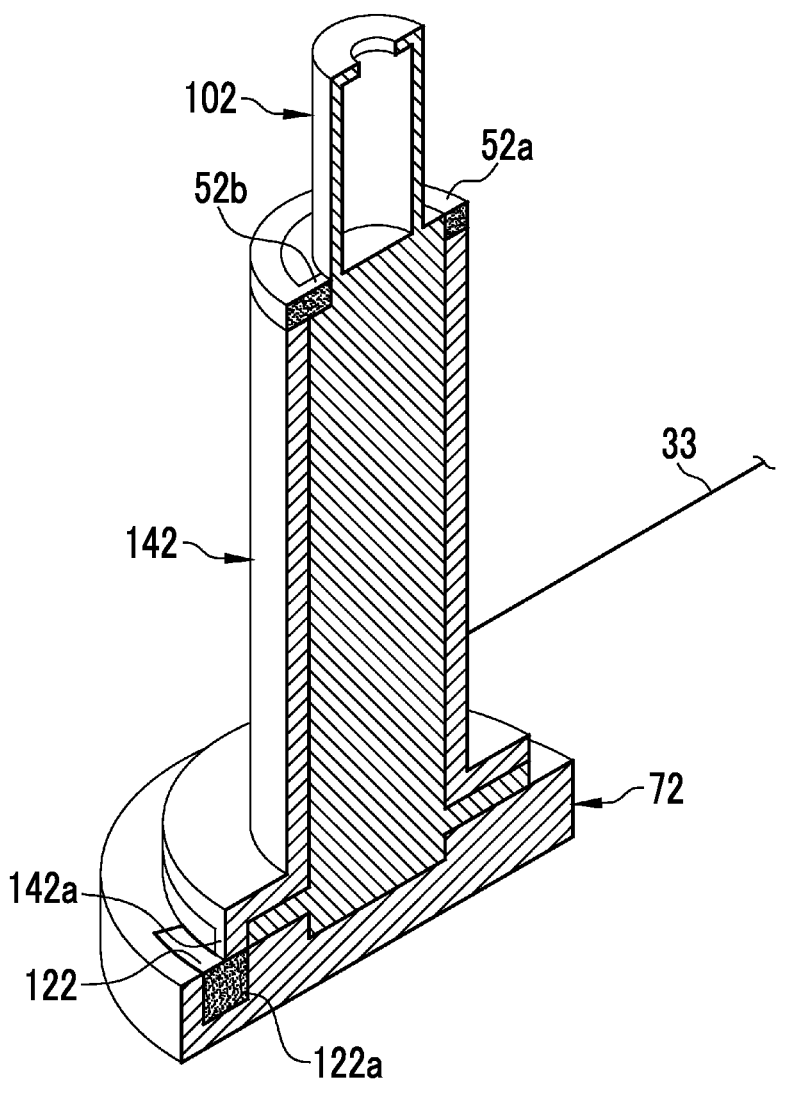
FIG. 9 is a diagram illustrating a mechanism in which rotational movement restriction of the wire pulling member is released in a process of attaching the angle knob.

As shown in FIG. 9, in a case where the second angle knob 52 is attached to the second wire pulling member 102 for the use of the endoscope 10, the second rotational movement restricting member 122 moves downward by being pressed by the second engagement ring 52a in the process of this attachment. Due to this movement, the second release protrusion 142a presses against the second rotational movement restricting protrusion 122a to move the second rotational movement restricting member 122 to the rotational movement allowing position. As a result, the restriction on the rotational movement of the second wire pulling member 102 is released. As described above, in the second embodiment, in the process of attaching the second angle knob 52, not only is the second angle knob 52 connected to the second wire pulling member 102, but also the restriction on the rotational movement of the second wire pulling member 102 is released at the same time.

EXPLANATION OF REFERENCES

10: endoscope
12: insertion part
12a: distal end
14: illumination window
16: observation window
18: forceps port
20: forceps outlet
30: bending part
31: first wire
32: second wire
33: third wire
34: fourth wire
40: operation part
40a: outer shell
50: rotational movement restricting member
51: first angle knob
51a: first engagement ring
51b: first protrusion
52: second angle knob
52a: second engagement ring
52b: second protrusion
100: wire pulling mechanism
61, 101: first wire pulling member
61a: first engagement groove
61b: first guide groove
62, 102: second wire pulling member
62a: second engagement groove
62b: second guide groove
70: tube body
71: middle plate
72: bottom plate
80: holder
81: first rotational movement restricting portion
82: second rotational movement restricting portion
111: first rotational movement restricting groove
112: second rotational movement restricting groove
121: first rotational movement restricting member
121a: first rotational movement restricting protrusion
122: second rotational movement restricting member
122a: second rotational movement restricting protrusion
131: first slide hole
132: second slide hole

141: first release member
141a: first release protrusion
142: second release member
142a: second release protrusion
CL: axis

What is claimed is:

1. An endoscope comprising:
an insertion part to be inserted into a body as an observation target;
a wire pulling member that pulls a wire disposed inside the insertion part in conjunction with a rotational movement to change a direction of a distal end of the insertion part;
an angle knob that is connected to the wire pulling member and transmits an operating force to the wire pulling member, wherein the angle knob is detached from the wire pulling member in a stage before use and is attached to the wire pulling member for use; and
a rotational movement restrictor engaged with the wire pulling member in a state in which the angle knob is detached from the wire pulling member, configured to restrict the rotational movement of the wire pulling member and to hold the wire pulling member in a predetermined rotational position,
wherein the wire includes a first wire, a second wire, the wire pulling member includes:
a first wire pulling member that is connected to the first and second wires and that selectively pulls one of the first and second wires according to a rotation direction.

2. The endoscope according to claim 1,
wherein the rotational movement restrictor in a stage for use is configured to detach from the wire pulling member, and the angle knob in the stage for use is configured to attach to the wire pulling member.

3. The endoscope according to claim 1,
wherein the rotational movement restrictor is provided so as to be movable between a rotational movement restricting position where the rotational movement restrictor is engaged with the wire pulling member to restrict the rotational movement of the wire pulling member and a rotational movement allowing position where the engagement is released and the rotational movement of the wire pulling member is allowed, and
the rotational movement restrictor moves from the rotational movement restricting position to the rotational movement allowing position by being pressed by the angle knob in a process of attaching the angle knob to the wire pulling member.

4. The endoscope according to claim 1,
wherein the wire pulling member is guided to the predetermined rotational position by being pressed by the rotational movement restrictor in a process of attaching the rotational movement restrictor.

5. The endoscope according to claim 1,
wherein:
the first wire that is pulled to allow the distal end of the insertion part to face a first direction; and
the second wire that is pulled to allow the distal end of the insertion part to face a second direction opposite to the first direction,
wherein the wire further includes:
a third wire that is pulled to allow the distal end of the insertion part to face a third direction perpendicular to the first direction; and
a fourth wire that is pulled to allow the distal end of the insertion part to face a fourth direction opposite to the third direction, the wire pulling member further includes:

a second wire pulling member that is connected to the third and fourth wires and that selectively pulls one of the third and fourth wires according to a rotation direction, and the angle knob includes:

a first angle knob that is connected to the first wire pulling member; and a second angle knob that is connected to the second wire pulling member.

6. The endoscope according to claim 5, wherein the rotational movement restrictor includes:

a first rotational movement restricting portion that restricts a rotational movement of the first wire pulling member; and a second rotational movement restricting portion that restricts a rotational movement of the second wire pulling member, and wherein restriction on the rotational movement of one of the first and second wire pulling members is released so that restriction on the rotational movement of the other is also released.

7. The endoscope according to claim 5, wherein the rotational movement restrictor consists of a first rotational movement restrictor that restricts a rotational movement of the first wire pulling member and a second rotational movement restrictor that restricts a rotational movement of the second wire pulling member, wherein in attaching the first angle knob, restriction on the rotational movement of the first wire pulling member by the first rotational movement restrictor is released, and wherein in attaching the second angle knob, restriction on the rotational movement of the second wire pulling member by the second rotational movement restrictor is released.

* * * * *